US009429547B1

(12) United States Patent
Kleinbaum et al.

(10) Patent No.: US 9,429,547 B1
(45) Date of Patent: Aug. 30, 2016

(54) SYSTEMS AND METHODS FOR AUTOMATED PREPARATION OF NUCLEIC ACIDS

(71) Applicant: Emerald Therapeutics, Inc., Menlo Park, CA (US)

(72) Inventors: Daniel J. Kleinbaum, Redwood City, CA (US); Brian M. Frezza, Redwood City, CA (US); Courtney E. Webster, Palo Alto, CA (US); Jonathan K. Leung, Sunnyvale, CA (US); Bradley M. Bond, Palo Alto, CA (US); George W. Fraser, San Francisco, CA (US); Alex M. Yoshikawa, San Mateo, CA (US); Shayna L. Hilburg, Menlo Park, CA (US); Eric Shyr, Menlo Park, CA (US); Kyla N. Velaer, Menlo Park, CA (US)

(73) Assignee: Emerald Therapeutics, Inc., South San Francisco, CA (US)

( * ) Notice: Subject to any disclaimer, the term of this patent is extended or adjusted under 35 U.S.C. 154(b) by 410 days.

(21) Appl. No.: 13/801,687

(22) Filed: Mar. 13, 2013

Related U.S. Application Data

(60) Provisional application No. 61/660,152, filed on Jun. 15, 2012.

(51) Int. Cl.
*C07H 21/00* (2006.01)
*C40B 50/00* (2006.01)
(Continued)

(52) U.S. Cl.
CPC .............. *G01N 30/02* (2013.01); *C07H 21/00* (2013.01); *C40B 50/00* (2013.01); *C40B 60/14* (2013.01)

(58) Field of Classification Search
None
See application file for complete search history.

(56) References Cited

U.S. PATENT DOCUMENTS 6,175,816 B1 * 1/2001 Flavin et al. ................... 506/36
6,238,927 B1    5/2001 Abrams et al.
(Continued)

FOREIGN PATENT DOCUMENTS

WO    WO 2008/097929 A2    8/2008

OTHER PUBLICATIONS

"Automated pilot scale purification of synthetic phosphorothioate oligonucleotides," Application Note by Amersham Biosciences, Oct. 1999.*

(Continued)

*Primary Examiner* — Samuel Woolwine
*Assistant Examiner* — Kaijiang Zhang
(74) *Attorney, Agent, or Firm* — Sheppard Mullin Richter & Hampton LLP

(57) ABSTRACT

A fabrication process for producing, annealing, and conjugating nucleic acid molecules is implemented, under the direction of one or more computer programs, on two or more instruments, for carrying out the process. The process can include: (a) synthesizing, on a solid support and in a plurality of reactions, at least one of a nucleic acid and a peptide nucleic acid, and cleaving the synthesized biomolecule product from the support, providing a sample of synthesized biomolecule product from each reaction of the plurality; (b) measuring, for each sample, the volume of the sample and/or the concentration of the product; (c) subjecting the product from each reaction to chromatography under conditions suitable for achieving single-base-resolution for the product, the conditions being a function of the volume and/or concentration measured in (b); and then (d) collecting and pooling, from the chromatography of (c) for each sample, peaks that correspond to the product.

19 Claims, 5 Drawing Sheets

(51) Int. Cl.
C40B 60/14 (2006.01)
G01N 30/02 (2006.01)

(56) References Cited

U.S. PATENT DOCUMENTS

| | | | |
|---|---|---|---|
| 6,448,387 | B1 | 9/2002 | Slater et al. |
| 7,501,253 | B2 | 3/2009 | Pourmand et al. |
| 7,538,202 | B2 | 5/2009 | Zhang et al. |
| 7,893,249 | B2* | 2/2011 | Bowman et al. .......... 536/25.31 |
| 2002/0119458 | A1 | 8/2002 | Suyama et al. |
| 2003/0152924 | A1 | 8/2003 | Ullman et al. |
| 2005/0075792 | A1 | 4/2005 | Shapiro et al. |
| 2005/0112065 | A1 | 5/2005 | Drummond et al. |
| 2007/0072215 | A1 | 3/2007 | Seelig et al. |
| 2009/0170719 | A1 | 7/2009 | Kazakov et al. |
| 2009/0191546 | A1 | 7/2009 | Zhang et al. |
| 2012/0100633 | A1 | 4/2012 | Manetto et al. |

OTHER PUBLICATIONS

Biswas et al., "Branch Migration Through DNA Sequence Heterology", J. Mol. Biol. (1998) 279, 795-806.
Braasch et al., "Locked nucleic acid (LNA): fine-tuning the recognition of DNA and RNA", Chemistry & Biology, 8 (2001) 1-7.
Doktycz, "Nucleic Acids: Thermal Stability and Denaturation," Encyclopedia of Life Sciences, pp. 1-18, John Wiley & Sons Ltd, Chichester. http://www.els.net [doi: 10.1038/npg.els.0003123] (Oct. 2002).
Dragulescu-Andrasi et al., "Cell-permeable GPNA with appropriate backbone stereochemistry and spacing binds sequence-specifically to RNA", Chem. Commun., 2005, 244-246.
Dragulescu-Andrasi et al., "A Simple-Backbone Modification Preorganizes Peptide Nucleic Acid into a Helical Structure", J. Am. Chem. Soc. 2006, 128, 10258-10267.
Freier et al., "The ups and downs of nucleic acid duplex stability: structure-stability studies on chemically-modified DNA:RNA duplexes", Nucleic Acids Research, 1997, vol. 25, No. 22, 4429-4443.
Frezza et al., "Modular Multi-Level Circuits from Immobilized DNA-Based Logic Gates", J. Am. Chem. Soc., 2007, 129, pp. 14875-14879.
International Search Report PCT/US2011/029947 dated Nov. 30, 2011.
Kahan et al., "Towards molecular computers that operate in a biological environment", Science Direct Physica D 237, (2008) 1165-1172.
Krane et al., "Time for DNA Disclosure", Science, vol. 326, Dec. 18, 2009, 1631-1633.
Kutyavin et al., "Oligonucleotides Containing 2-Aminoadenine and 2-Thiothymine Act as Selectively Binding Complementary Agents", Biochemistry 1996, 35, 11170-11176.
Laplanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates," Nucleic Acids Res. 14(22):9081-9093 (1986).
Latimer et al., "Synthetic repeating sequence DNAs containing phosphorothioates: nuclease sensitivity and triplex formation," Nucleic Acids Res. 17(4):1549-1561 (1989).
Lee et al., "Chitosan: a novel platform in proton-driven DNA strand rearrangement actuation", Mol. BioSyst. 2009, 5, 391-396.
Li et al., "A new class of homogeneous nucleic acid probes based on specific displacement hybridization", Nucleic Acids Research, 2002, vol. 30, No. 2, e5, 9 pages.
Lusvarghi, et al., "Loop and backbone modifications of peptide nucleic acid improve G-Quadruplex binding selectivity", JACS, 131, 18415-18424, (2009).
Maugh II, "Wolf & Lamb Chemistry, Many useful reactions difficult to perform by conventional means can be carried out easily with polymeric reagents", Science, vol. 217, Aug. 20, 1982, pp. 719-720.
Nielsen et al., "An Introduction to Peptide Nucleic Acid", Current Issues Molec. Biol. (1999), 1(2): 89-104.
Nishikawa, et al., "DNA computation simulator based on abstract bases", Soft Computing 5: 25-38, (2001).
Ortega et al., "Binding Affinities of Oligonucleotides and PNAs Containing Phenoxazine and G-Clamp Cytosine Analogues Are Unusually Sequence Dependent", Organic Letters, 2007, vol. 9, No. 22, 4503-4506.
Panyutin et al., "Formation of a Single Base Mismatch Impedes Spontaneous DNA Branch Migration", J. Mol. Biol. (1993), 230, 413-424.
Panyutin et al., "The kinetics of spontaneous DNA branch migration", Proc. Natl. Acad. Sci., USA, vol. 91, pp. 2021-2025, Mar. 1994.
Picuri et al., "Universal Translators for Nucleic Acid Diagnosis", J. Am. Chem. Soc. 2009, 131, 9368-9377.
Pon, "Solid-Phase supports for Oligonucleotide synthesis", Methods in Molecular Biology, vol. 20, pp. 465-496, (1993).
Sager, et al., "Designing nucleotide sequences for computation: A survey of constraints", DNA11, LNCS 3892: 275-289, (2006).
Sahu et al., "Synthesis of Conformationally Preorganized and Cell Permeable Guanidine-Based-Peptide Nucleic Acids (GPNAs)", J. Org. Chem. 2009, 74, 1509-1516.
Seelig et al., "Enzyme-Free Nucleic Acid Logic Circuits", Science, vol. 314, Dec. 8, 2006, pp. 1585-1588.
Summerton et al., "Review Article Morpholino Antisense Oligomers: Design, Preparation, and Properties", Antisense and Nucleic Acid Drug Development 7: 187-195 (1997).
Tajima et al., "Direct Oxidative Cyanation Based on the Concept of Site Isolation", J. Am. Chem. Soc. 2008, 130, 10496-10497.
Uhlmann, et al., "PNA: Synthetic polyamide nucleic acids with unusual binding properties", Agnew. Chem. Int. Ed., 37: 2796-2823, (1998).
Uhlmann, et al., "Synthesis and properties of PNA/DNA Chimeras", Angew. Chem. Int, Ed. Engl., 35, No. 22, 2632-2635, (1996).
Voelcker et al., "Sequence-Addressable DNA Logic", Small 2008, 4, No. 4, pp. 427-431.
Voit, "Sequential One-Pot Reactions Using the Concept of Site Isolation", Angew. Chem. Int. Ed. 2006, 45, 4238-4240.
Yashin et at "Networking Particles over Distance Using Oligonucleotide-Based Devices", J. Am. Chem. Soc., 2007, 129, 15581-15584.
Zhang et al., "Control of DNA Strand Displacement Kinetics Using Toehold Exchange", J. Am. Chem. Soc., 2009, 131, 17303-17314.
Zhang et al., "Engineering Entropy-Driven Reactions and Networks Catalyzed by DNA", Science, vol. 318, Nov. 16, 2007, 1121-1125.
Zhou et al., "Novel Binding and Efficient Cellular Uptake of Guanidine-Based Peptides Nucleic Acids (GPNA)", J. Am. Chem. Soc. 2003, 125, 6878-6879.
Wenska, et al., "An activated triple bond linker enables 'click' attachment of peptides to oligonucleotides on solid support," (2011), 39(20):9047-9059.

* cited by examiner

SYSTEMS AND METHODS FOR AUTOMATED PREPARATION OF NUCLEIC ACIDS

CROSS-REFERENCE TO RELATED APPLICATIONS

This application claims the benefit under 35 U.S.C. §119(e) to U.S. provisional application Ser. No. 61/660,152, filed Jun. 15, 2012, the contents of which are incorporated by reference here in its entirety.

BACKGROUND

Nucleic acids have been used to implement nano-scale information processing systems suitable for solving computational problems in a test tube or a cell. Such nano-scale systems can be compatible with biological environments and have the potential for use in the diagnosis and treatment of complex diseases, among other applications.

A nano-scale information processing system of suitable capability for such uses requires a myriad of nucleic acid segments, serving as computation units, and concatenated polynucleotides to carry out logic operations. This requirement is dependent upon synthesizing a large number of nucleic acids at a high purity and conjugating or annealing them in an efficient, well-controlled fashion.

SUMMARY

Provided, in some embodiments, is a system comprising at least two instruments and one or more computer programs that, when executed, configure the system to: (a) synthesize, on a solid support and in a plurality of reactions, at least one of a nucleic acid (NA) and a peptide nucleic acid (PNA), and cleave the synthesized biomolecule product from said solid support, thereby providing a sample of synthesized biomolecule product from each reaction of the plurality; (b) measure, for each sample, the volume of the sample and/or the concentration of the synthesized biomolecule product; (c) subject the synthesized biomolecule product from each reaction to chromatography under conditions suitable for achieving single base-resolution for the synthesized biomolecule product, wherein the conditions are a function of the volume and/or concentration measured in step (b); and then (d) collect and pool, from the chromatography of (c) for each sample, peaks that correspond to the synthesized biomolecule product, wherein each of the instruments effects at least one of (a)-(d) under direction of the computer programs.

In some embodiments, the instruments are interconnected, or alternatively are connected to a central computer. In some embodiments, the instruments access a data file or a database at the central computer. In some embodiments, the instruments are controllable by the central computer.

In some embodiments, the system is further configured to desalt and dry the collected and pooled synthesized biomolecule product and to dissolve the product in a buffer or solvent.

In some embodiments, the synthesized biomolecule product is attached to said solid support through a linker.

In some embodiments, the conditions are further determined with properties of the synthesized biomolecule product. Non-limiting examples of properties of the synthesized biomolecule product include chemical composition, number of bases, presence or absence of linkers, modifications, and/or secondary structure.

In some embodiments, the system is configured to introduce a modification to the synthesized biomolecule product, which modification includes, without limitation, addition of one or more selected from the group consisting of a fluorescent molecule, a fluorescence quenching molecule, a non-standard base, a non-nucleic acid based molecule, and a functional group.

In some embodiments, the system is further configured to remove a protection group from the synthesized biomolecule product, wherein the protection group is added during synthesis or is part of the individual monomers used as reactants in the synthesis of the biomolecule. For instance, the protection group can be acetyl (Ac), benzoyl (Bz), isobutyryl (iBu), dimethylformamidine (dmf), pivaloyl (Piv), benzhydryloxycarbonyl (Bhoc), fluorenylmethyloxycarbonyl (Fmoc), tert-butyloxycarbonyl (Boc), carboxybenzyl (Cbz), 2-chlorocarboxybenzyl (2-Cl-Cbz), trityl (Trt), methoxytrityl (Mtr), pentamethyldihydrobenzofuran (Pbf), S-tert-butyl (S-tBu), acetamidomethyl (Acm), and tert-butyl (tBu).

In some embodiments, the system is further configured to incubate a first synthesized biomolecule product with a second synthesized biomolecule product under conditions such that the first synthesized biomolecule product anneals with the second synthesized biomolecule product. In some embodiments, the system is further configured to incubate a first synthesized biomolecule product with a second synthesized biomolecule product under conditions such that at least one covalent bond is formed between the first synthesized biomolecule product and the second synthesized biomolecule product, forming a conjugated product. In some embodiments, the incubation further involves a linker that facilitates the formation of one or more covalent bonds between the first synthesized biomolecule product and the second synthesized biomolecule product. In some embodiments, the system is further configured to attach the first synthesized biomolecule product to a solid support prior to the incubation. In some embodiments, the system is further configured to pass the conjugated product though chromatography under conditions suitable for separating the conjugated product from unconjugated first and second biomolecule products.

In some embodiments, the first and second synthesized biomolecule products are selected from the group consisting of (1) a NA and a NA, (2) a NA and a PNA, (3) a PNA and a NA and (4) a PNA and a PNA.

The chromatography can be selected, without limitation, from high pressure liquid chromatography (HPLC), medium pressure liquid chromatography, low pressure liquid chromatography or fast protein liquid chromatography (FPLC).

In some embodiments, the system is further configured to determine the purity and/or identity of the biomolecule product. The determination, for instance, is made by a method selected from the group consisting of mass spectrometry, liquid chromatography, capillary and gel electrophoresis, absorbance, fluorescence and infrared spectroscopy, job plots, melting point analysis, mass, and fluorescence polarization.

In some embodiments, the reactions of the plurality are carried out in a 96-well plate, a 384-well plate, a solid phase extraction cartridge, solid phase synthesis columns, or vials.

In some embodiments, the program code is coded in a symbolic lab language. The symbolic lab language, in some embodiments, specifies workflow management that comprises sample tracking, data management and manipulation, instrument management, and conditional analysis of the process.

BRIEF DESCRIPTION OF THE DRAWINGS

The figures of the accompanying drawings describe provided embodiments by way of illustration only, in which.

Figure 1:
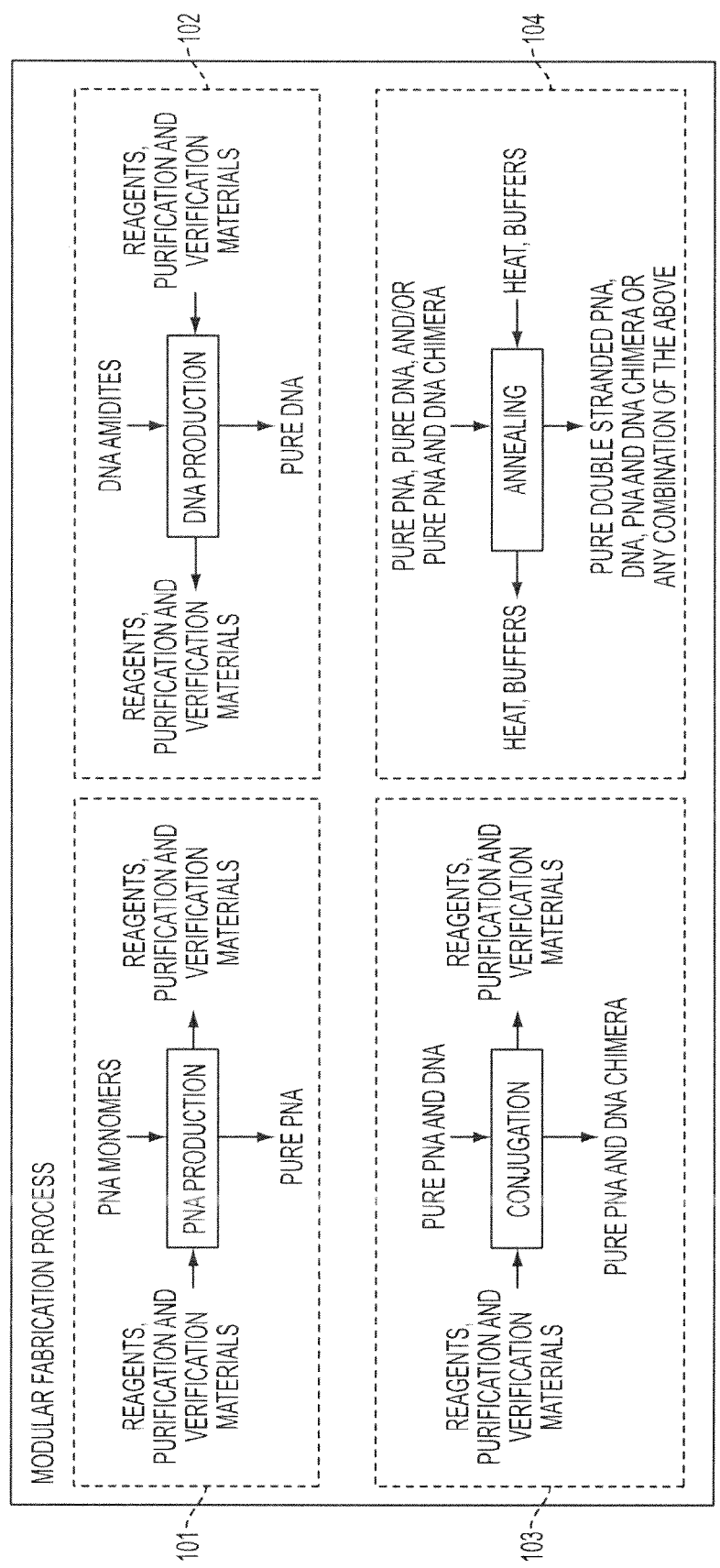
FIG. 1 depicts the modules of the inventive fabrication process.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow.

DETAILED DESCRIPTION

This specification describes a fabrication process for the production, purification, annealing, quality control, quality assurance and conjugation of nucleic acid molecules, a category that includes, without limitation, ribonucleic acids (RNA), deoxyribonucleic acid (DNA), peptide nucleic acids (PNA) and their derivatives. In certain embodiments the phrase "nucleic acid" refers to RNA and DNA only.

The described fabrication process can be automated. In that context each step of the fabrication process can be carried out by different instruments, the steps among them being coordinated such that the need for human intervention is minimized or eliminated. To this end, the instruments are interconnected or, alternatively, are each connected to a central computer, directly or over a computer network. Each of the instruments can run its own computer program to carry out its function; in any event, their functions are coordinated to effect workflow management of the fabrication process. The coordination can be implemented with one or more computer programs that direct such coordination, optionally with the involvement of associated data, which is stored in or accessed by the system. These computer programs can be located centrally on a computer server, or they also can be distributed across the network of instruments and computers. Likewise, the data can be stored on a computer server or distributed among different instruments and computers. The workflow management can include, for instance, sample tracking, data management and manipulation, instrument management, and conditional analysis of the process.

An automated process is not limited to just carrying out a series of predetermined steps. In contrast, the process checks and monitors certain steps, such as the input and output of the steps, and determines whether, when, and how a later step is carried out, to ensure the completion and to optimize the output of the process. To this end, suitable computer programs and/or languages can be used, not only to implement taking measurements and making measurement-based decisions but also to provide an interface for the scientists to monitor the overall process and conduct troubleshooting. A suitable program language could, for instance, facilitate communication with lab instruments and provide user-friendly interface, particularly for process monitoring and data visualization. One such example is the Mathematica® 8 language provided by Wolfram Research (Champaign, Ill.). As described further below, moreover, to this end the present inventors developed a software package called "Symbolic Lab Language" (SLL), based on the Mathematica® language.

In some embodiments the fabrication process is modular, in the sense that a collection of certain steps form a module and the steps within a module are automated, whereas automation between modules is optional. For instance, the fabrication process can include a nucleic acid synthesis module (e.g., FIG. 1, modules 101 and 102, and FIGS. 2-3), a conjugation module (e.g., FIG. 1, module 103, and FIG. 4) and an annealing module (e.g., FIG. 1, module 104, and FIG. 5), and the modules are coordinated in a way as illustrated in FIG. 1.

I. Nucleic Acid Synthesis

In one aspect the present disclosure provides a system for carrying out a process to synthesize a nucleic acid. The system can include, for example, at least two instruments and one or more computer programs that, when executed, configure the system to:

(a) synthesize, on a solid support and in a plurality of reactions, at least one of a nucleic acid, and cleave the synthesized biomolecule product from said solid support, thereby providing a sample of synthesized biomolecule product from each reaction of the plurality;

(b) measure, for each sample, the volume of the sample and/or the concentration of the synthesized biomolecule product;

(c) subject the synthesized biomolecule product from each reaction to chromatography under conditions suitable for achieving up to single base-resolution for the synthesized biomolecule product, wherein the conditions are a function of the properties of the biomolecule (including but not limited to its sequence of nucleobases, non-nucleobase modifiers such as fluorophores or fluorescence quenchers, and secondary structure), the volume, and/or the concentration measured in step (b); and then (d) collect and pool, from the chromatography of (c) for each sample, peaks that correspond to the synthesized biomolecule product, wherein each of the instruments effects at least one of (a)-(d) under direction of the computer programs. In one aspect, the system further desalts and dries the collected and pooled synthesized biomolecule product and dissolves the product in a buffer or solvent.

In accordance with this description, nucleic acids can be PNA, conventional nucleic acids (NA), such as DNA and RNA or other nucleic acid derivatives like gamma-PNA, LNA, or GNA. Unlike DNA and RNA, PNA and their derivatives rely on amide bonds to link the individual monomers together. Instead of phosphoramidite chemistry, therefore, amide bonding forming conditions and coupling reagents like HBTU are employed to make strands of these monomers. Conventional methodology for making PNA and PNA-like oligonucleotides is disclosed, for instance, in Beck, "Solid Phase Synthesis of PNA Oligomers," METHODS IN MOLECULAR BIOLOGY, 1, Volume 208, Peptide Nucleic Acids, II, pages 29-41, the contents of which are incorporated into the present disclosure in their entirety by reference.

The synthesized nucleic acid can be at least 3 bases long, for instance. Alternatively, they can be at least 4, 5, 6, 7, 8, 9, 10, 11, 12, 13, 14, 15, 16, 17, 18, 19, 20, 21, 22, 23, 24, 25, 30, 35 or 40 bases long. In a given embodiment the synthesized nucleic acid can be as long as 20 bases or, alternatively, as long as 25, 30, 35, 40, 45, 50, 60, 70, 80, 90, 100, 110, or 120 bases.

Synthesis

Solid support-based nucleic acid synthesis techniques are known (see, e.g., Pon "Solid-phase supports for oligonucleotide synthesis," *Methods in Molecular Biology* (Totowa, N.J., United States) (1993) 20 (Protocols for Oligonucleotides and Analogs) pages 465-496). Thus, the nucleic acid can be synthesized de novo, where each nucleotide is sequentially coupled to the growing nucleic acid chain (e.g., FIG. 2, step 211 and FIG. 3, step 311).

In some embodiments the process introduces a modification to the synthesized biomolecule product. The modification can comprise addition of one or more selected from the group consisting of a fluorescent molecule, a fluorescence-quenching molecule, a non-standard base, a non-nucleic acid based molecule, and a functional group.

The biomolecule product can be synthesized on the solid support while connected to the support through a linker. Exemplary solid support materials include controlled pore glass (CPG) and macroporous polystyrene (MPPS). Illustrative of suitable linkers are non-nucleosidic linkers and nucleoside succinates. Once synthesized, the nucleic acid molecule can be cleaved from the solid support (FIG. 2, step 212 and FIG. 3, step 312).

The biomolecule product can be synthesized with a protection group or groups. Non-limiting examples of protecting groups include acetyl (Ac), benzoyl (Bz), isobutyryl (iBu), dimethylformamidine (dmf), pivaloyl (Piv), benzhydryloxycarbonyl (Bhoc), fluorenylmethyloxycarbonyl (Fmoc), tert-butyloxycarbonyl (Boc), carboxybenzyl (Cbz), 2-chlorocarboxybenzyl (2-Cl-Cbz), trityl (Trt), methoxytrityl (Mtr), pentamethyldihydrobenzofuran (Pbf), S-tert-butyl (S-tBu), acetamidomethyl (Acm), and tert-butyl (tBu). In one embodiment the process further includes removing the protection group(s) from the synthesized biomolecule product (FIG. 2, step 212 and FIG. 3, step 312).

Figure 2:
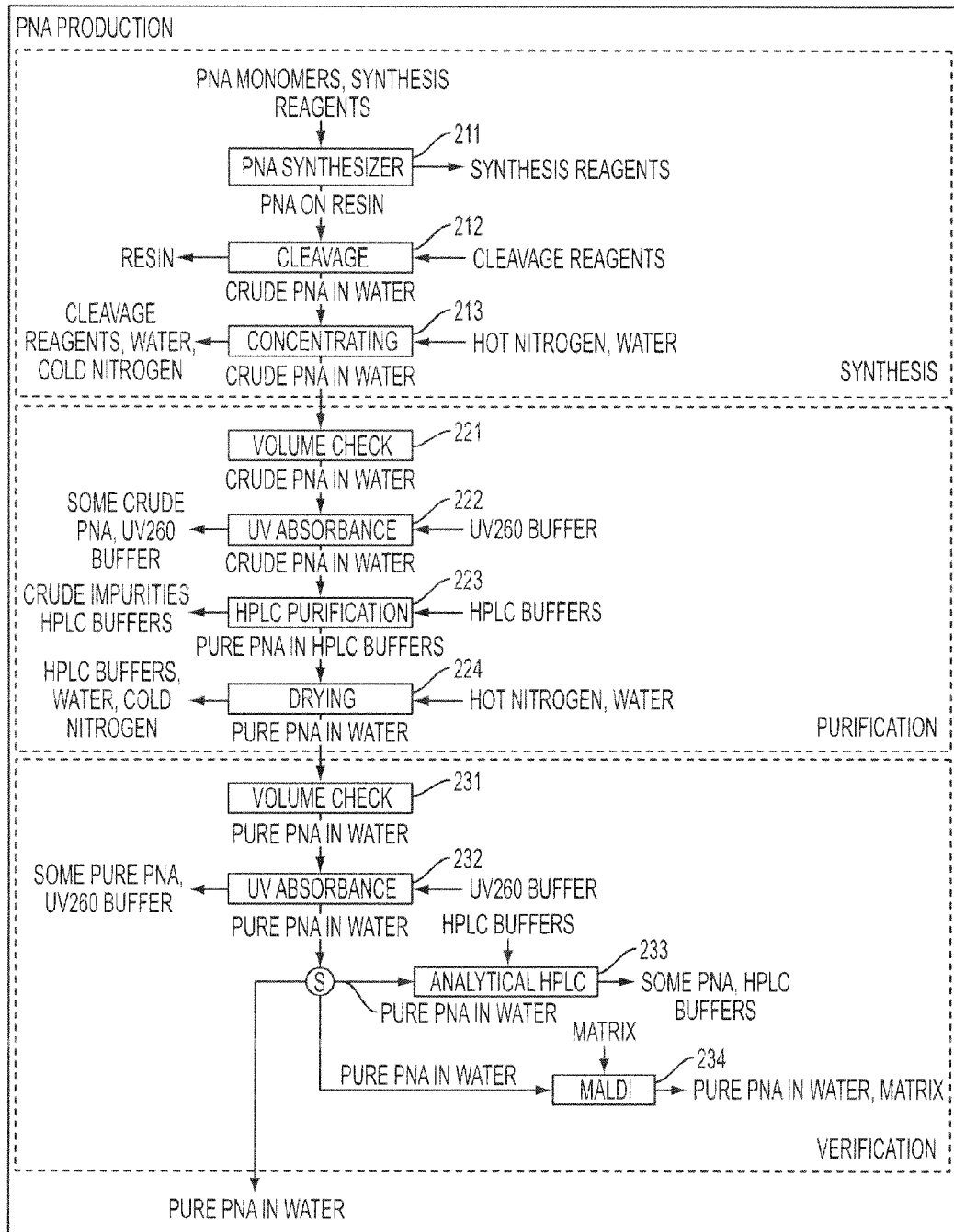
FIG. 2 shows an automated process for peptide nucleic acid (PNA) production.
Figure 3:
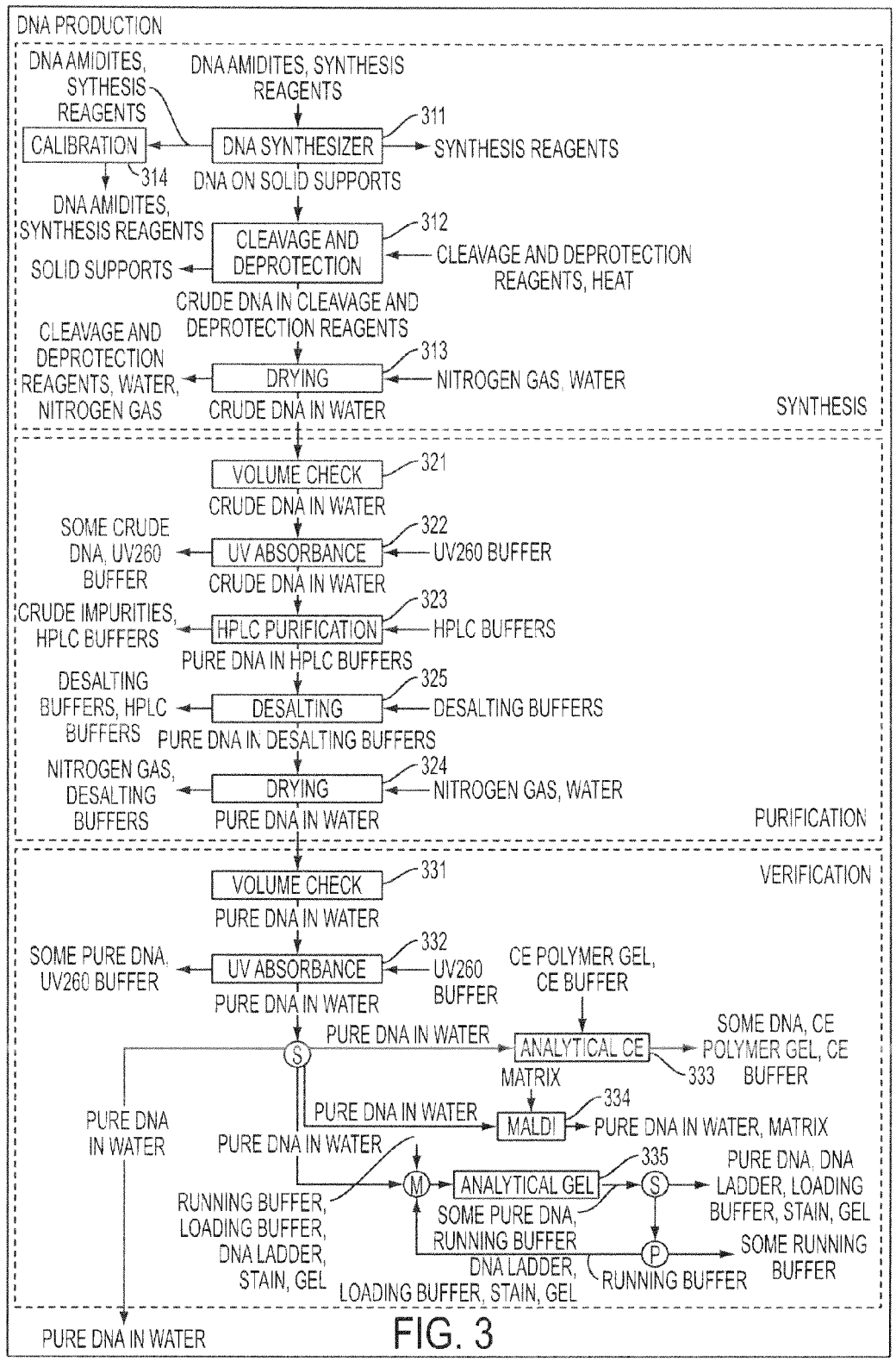
FIG. 3 illustrates an automated deoxyribonucleic acid (DNA) and ribonucleic acid (RNA) production process.

The synthesized biomolecule product can be desalted and concentrated, using, for instance, hot or room temperature nitrogen gas (for example, see FIG. 2, step 213, and FIG. 3, step 313). The concentrated or dried product then is ready for purification.

Optionally, reagents eluted from the nucleic acid synthesis reaction, such as DNA phosphoramidites and synthesis reagents, are analyzed to calibrate the nucleic synthesis system (FIG. 3, step 314). Nucleic acid synthesis can be carried out in any conventional containers, such as solid phase extraction cartridges, solid phase synthesis columns, or vials, and is preferably carried out in multiple reactions in parallel to achieve high production rate and high production volume. For instance, 96-well plates and 384-well plates are suitable formats for this purpose, as are instruments that can run parallel reactions in multiple containers like the aforementioned cartridges and containers. An example of one such instrument is an ABI 3900 DNA/RNA Synthesizer.

Purification and Process Control

The synthesized biomolecule product is subject to purification, as described above. In general, the purification step should be optimized such that only the nucleic acid of the desired length and modification is retained and the other components are removed, such as incompletely synthesized nucleic acids. In other words, if the purification separates the completely synthesized product from incompletely synthesized products, the separation should have a single-base resolution, since some of the incomplete products may be only one base shorter than the desired complete product.

In accordance with this aspect of the present description, conditions for the purification are determined based on certain parameters of the synthesized biomolecule product. One such parameter is the volume of the synthesized biomolecule product and another is its concentration. Accordingly, in one embodiment the system is configured to measure the volume (FIG. 2, step 221, and FIG. 3, step 321) of the biomolecule sample and/or the concentration (FIG. 2, step 222, and FIG. 3, step 322) of the biomolecule product in the sample.

An illustrative approach to volume checking entails the use of a BioMicroLab VolumeCheck (BioMicroLab, Concord, Calif.), which can perform liquid-level detection on a 96 well plate. To analyze the concentration, a serial dilution of a small amount of the sample can be loaded into UV plates, followed by determination of UV absorbance (FIG. 2, step 222, and FIG. 3, step 322). The concentration of the nucleic acid then is calculated from the UV absorbance.

Yet another parameter to consider when optimizing the purification conditions is the properties of the biomolecule product. Non-limiting examples of such properties are the chemical composition, number of bases, presence or absence of linkers, modifications, and the secondary structure of the biomolecule product.

The purification method can employ chromatography, which includes, for instance, high pressure liquid chromatography (HPLC), medium pressure liquid chromatography, low pressure liquid chromatography and fast protein liquid chromatography (FPLC) (FIG. 2, step 223 and FIG. 3, step 323).

Along with any and preferably all of such parameters, the system can determine the purification conditions. In the case of HPLC, for example, the conditions include types of equilibration buffer and elution buffer, buffer concentrations, the pH of the buffers, loading gradients, loading pressure, types and sizes of column, and running time. For instance, purification of a synthesized DNA product by ion-exchange HPLC can use 20 millimolar Tris base buffers with different amounts of salt (sodium chloride) with a gradient that runs for one hour on a Dionex DNAPac PA200 column to produce single base resolution of the synthesized product. If the DNA product has secondary structure, the pH of these buffers can be raised to disrupt those structures and produce a more consistent chromatogram.

At such determined conditions, the samples pass the chromatography, and the peaks that correspond to the synthesized biomolecule product are collected and pooled, desalted and concentrated (e.g., FIG. 2, step 224, and FIG. 3, steps 324 and 325).

Optionally, the synthesized and purified nucleic acid is subject to volume check (FIG. 2, step 231 and FIG. 3, step 331), concentration check (FIG. 2, step 232 and FIG. 3, step 332) and further verification and quality control using, e.g., mass spectrometry, liquid chromatography, capillary and gel electrophoresis, absorbance, fluorescence and infrared spectroscopy, job plots, melting point analysis, mass, or fluorescence polarization. Examples of verification methods include, without limitation, analytical capillary electrophoresis (CE) (FIG. 2, step 233 and FIG. 3, step 333), matrix-assisted laser desorption/ionization (MALDI) (FIG. 2, step 234 and FIG. 3, step 334) and analytical gel (FIG. 3, step 335).

The process of the present disclosure achieves high purification and high recovery rate. The overall yield can depend on the length of the nucleic acid synthesized and the scale of the fabrication. The recovery rate at each step is typically above about 90%, however. In one aspect, it is contemplated that the overall recovery rate is at least about 70%, after the multiple steps of desalting, chromatography, concentration. Even higher recovery rates, such as 75%, 80%, 85% or 90%, can be reached in some embodiments.

In another aspect, the collected final nucleic acid product contains less than 0.01% contaminant nucleic acids, including incompletely synthesized or modified nucleic acid molecules. In some aspect, the contamination is less than about 0.02%, 0.05%, 0.1%, 0.5%, or 1%.

In yet another aspect, the disclosed process achieves high production yields. For instance, one run of the process can produce about 25 nanomoles of nucleic acid. Alternatively, the production volume can be at least about 50 nanomoles, 100 nanomoles, 200 nanomoles, 500 nanomoles, 1 µmoles, 10 µmoles, 100 µmoles, 1 micromoles, or 10 micromoles per run.

II. Conjugation

The system can be configured to conjugate two or more nucleic acids. These can be prepared by the system itself, by way of an earlier step, or can be obtained elsewhere. Such conjugated products can be chimeric oligonucleotides, which are oligonucleotide strands that contain different backbone chemistries in the same molecule, or conjugated products could be composed of strands of the same backbone chemistry conjugated together. For example, a strand designed to consist of half PNA backbone and half DNA backbone would require a way to join these different backbone chemistries.

There is conventional methodology for making these chimeric strands. Thus, with respect to the foregoing example of a PNA/DNA chimera, the difference in chemistries can be bridged by using modified DNA or PNA monomers. For DNA the 5'-dimethoxytrityl (DMT) protected hydroxyl is replaced with a monomethoxytrityl (MMT)-protected amine that can react with the carboxylic acid of a PNA after deprotection. For PNA the protected N-terminal nitrogen is replaced with a DMT-protected hydroxyl that can react with the phosphoramidite group on DNA after deprotection. These approaches are further described, for instance, in Uhlmann, et al., *Angew. Chem.* (Int'l ed.) 37: 2796-823 (1998). The methodology is not limited to the examples provided here but can consist of any chemistry that facilitates a covalent bond between the subgroups of the chimera.

In some embodiments the conjugated nucleic acid molecules can be (1) a NA and a NA, (2) a NA and a PNA, (3) a PNA and a NA or (4) a PNA and a PNA. The NA and PNA portions can also contain non-NA modifications (such as fluorophores, quenchers and other non-NA components), linkers, and functional groups. The method also can entail conjugating already conjugated products with more nucleic acid molecules, whether alone or in conjugated forms.

Figure 4:
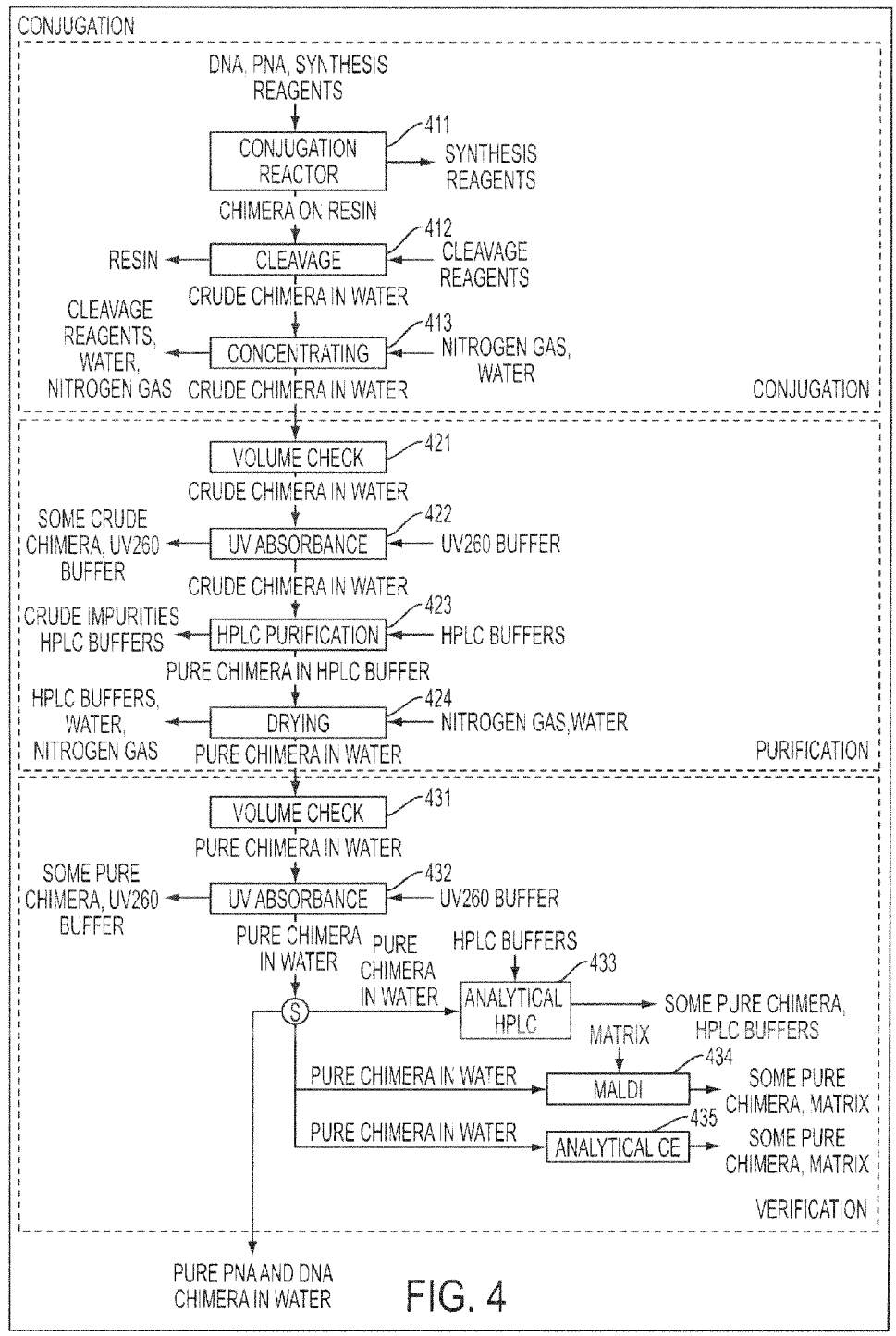
FIG. 4 renders an automated conjugation process.

Accordingly, the conjugation process can entail incubating a first nucleic acid or a conjugated product with a second nucleic acid or conjugated product under conditions such that at least one covalent bond is formed between them, forming a conjugated product (FIG. 4, step 411). By way of illustration, one of the nucleic acids can be anchored on a solid support, optionally through a linker. Upon completion of the conjugation reaction, the conjugated product is cleaved from the solid support (FIG. 4, step 412) and concentrated (FIG. 4, step 413).

The incubation can involve a NA or non-NA based linker that facilitates the formation of one or more covalent bonds between the nucleic acids.

As in the process for nucleic acid synthesis, the conjugated product then is subject to purification (FIG. 4, steps 421-424). Also as in the nucleic acid synthesis process, the purification conditions can be optimized, taking into consideration the volume of the sample and/or the concentration and/or the properties of the conjugated product. The purified products are then subject to desalting (not shown) and verification (FIG. 4, steps 431-435).

III. Annealing

Figure 5:
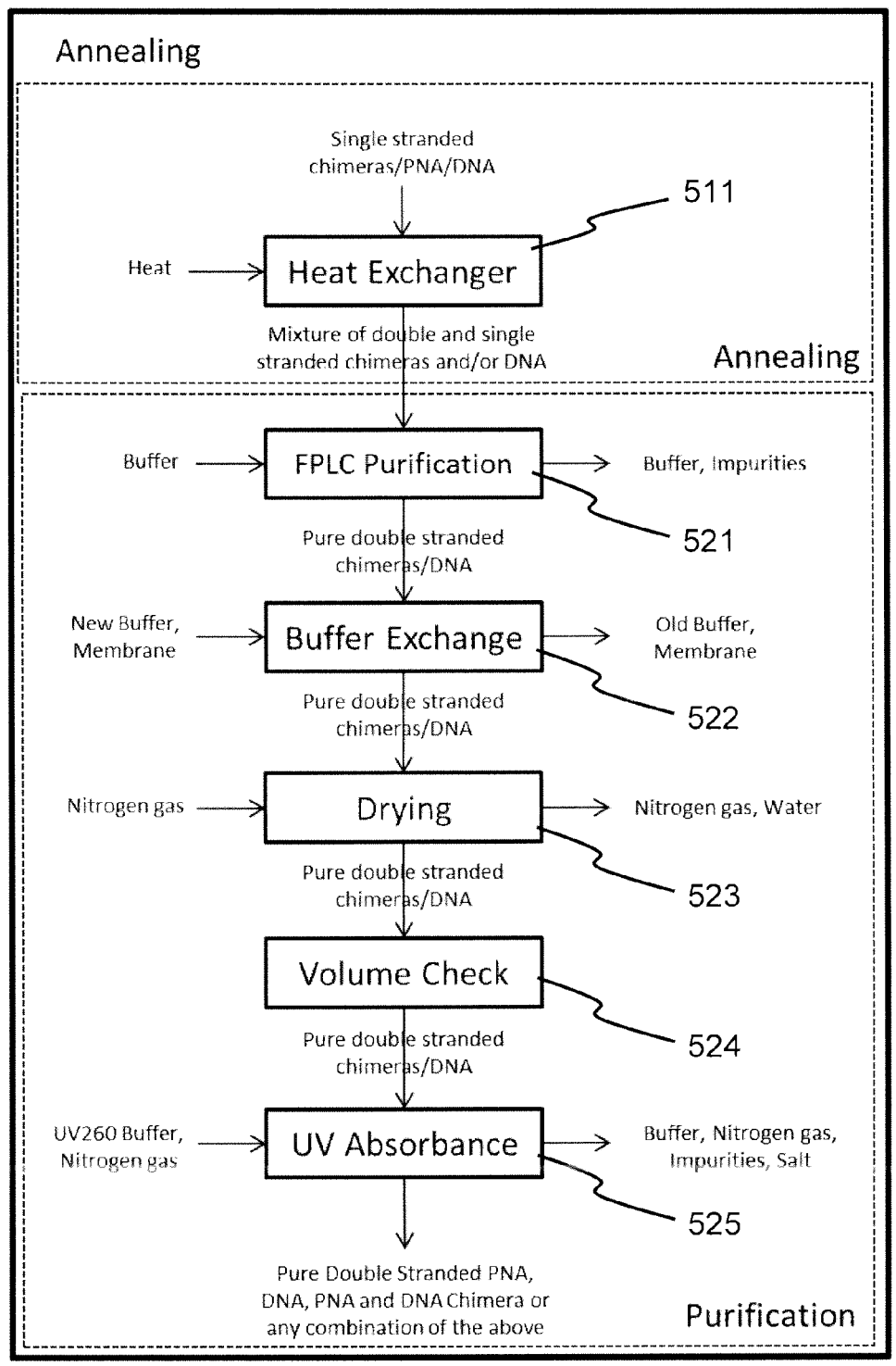
FIG. 5 depicts an automated annealing process.

Automated annealing processes are provided, too, carried out alone or following the nucleic synthesis and/or conjugation processes. The annealing process can entail incubating a first nucleic acid with a second nucleic acid under conditions such that the first nucleic acid anneals with the second nucleic acid (FIG. 5, step 511). Upon annealing, the purification and verification process (illustrated in FIG. 5, steps 521-525) are similar to those in the synthesis and conjugation processes.

IV. Computer Programs

In its other aspects, the present description provides a fabrication process that entails synthesis, purification, conjugation and/or verification of nucleic acids. Each step in the process may be carried out by a different instrument, but the various devices and steps are coordinated to achieve a high level of automation, preferably complete automation without human intervention. Such coordination can be implemented with a centralized computer, which is connected, directly or through a computer network, to the computers of the instruments that perform each step. A centralized computer is not required, however. Thus, in an alternative embodiment the coordination is implemented through program code and/or data that direct the overall fabrication process and that are accessible to each of the instruments. Such program code and/or data do not have to be centrally located, as noted above. In this context it is adequate to implement the fabrication process with control effected via a distributed system, which collectively contains the program code and/or data. Without the need of an expensive computer server, moreover, such a distributed system may be more cost-effective than a system that requires such a computer server.

As an integral part of the system, software programs that run on the computer or in other part of the system are also provided in the present disclosure. The software program implements workflow management that include, without limitation, sample tracking, data management and manipulation, instrument management, and progress tracking and modification of the process.

In some embodiments, the system includes a computer program that enables virtual network computing (VNC), as generally described. Pursuant to VNC, operations at some or all of the instruments in the system can be monitored and/or controlled from any computer connected to the system.

In a particular aspect, the software program is coded in the Mathematica® language or more particularly a symbolic lab language (SLL) package developed by the present inventors, although any computer language can be used.

Symbolic Lab Language

Data Integration

SLL offers an objective system for querying, manipulating, and displaying experimental results. The results of each experiment, including data points involved in plots (such as chromatographs or spectra etc.), images (such as gels, blots and microscope slides), and meta data (such as the date the experiment was performed, the reagents used in the course of the experiment, the instrument utilized to conduct the experiment etc.) can be all processed and inserted into an SQL database and then linked together by a shared pointer or "key" which can be used to simultaneously extract that information from the database and presented in the form of a single computational object that can then be passed as inputs to functions to display, process or query their objectives.

This allows scientists easily and compactly to share data across multiple notebooks and teams without losing quantitative precision or any associated details. This is analogous to the way biologists use the Protein Databank (PDB) to share information. Given only the accession number to the PDB, a scientist can share the complete set of information regarding a given protein crystallization. Likewise, SLL data integration follows the same concept, i.e., it is a single platform for compactly uniting and sharing all experimental data accumulated in a given laboratory or facility.

Furthermore, a computational system of data objects per SLL allows one to manipulate large sets of experimental data abstractly, by giving one the ready ability to write functions that accept these objects as inputs and process them in an algorithmic manner.

Objects of SLL can be defined such as:

data[integer,<type>]—(e.g., data[44, NMR] can point to the 44th nuclear magnetic resonance (NMR) experiment performed in the lab, and data[1023, MALDI] refers to combined results from the 1,023rd matrix-assisted laser desorption/ionization (MALDI) experiment performed.

Examples of functions are:

info[ ]—calling info on a data object (i.e., info[data[44, NMR]] connects to our SQL database and then returns a list of all data associated with that experiment in the form of replacement rules. It also has the side effect of locally caching that data into RAM as further calls to info[ ] will shortcut to the local copy if it already exists (for faster execution times); and inform[ ]—calling inform on a list of all data associated with the experiment in the form of replacement rules will: check to see if that data has already been inserted into the database and, if so, return the data[ ] object previously inserted and otherwise will insert that data into the database and return a new data[ ] pointer to that object.

Sample Integration

SLL also includes a computational object for tracking and querying the complete history of laboratory samples. Tracked information includes: information about source materials; preoperative information from processes involved in its creation; its present properties, such as experiments it which it has been used; quality assurance (QA) information; information regarding its properties, such as volume, concentration and pH; information regarding its innate properties, such as chemical composition, and physical location in the laboratory or facility.

Here an object can be:

sample["sample name",<type>]—sample["Nearest Neighbor Strand 4","Pure DNA"]. refers to large lists of information involving that sample such as materials involved in their creation, dates and experimental results from production experiments involved, attributes of the sample, such as its volume, pH, concentration, and its physical location in the lab (where it is stored); or group["name of group"]—(e.g., group["Nearest Neighbor Strands"] refers to a collection of samples that you wish to manipulate in bulk. Groups can refer to any size collection of samples, and samples can be members of multiple groups).

Examples of functions are:

info[ ]—calling info on a data object (i.e. info[sample ["Nearest Neighbor Strand 5",DNA]] connects to our SQL database and then returns a list of all data associated with that experiment in the form of replacement rules. It also has the side effect of locally caching that data into RAM as further calls to info[ ] will shortcut to the local copy if it already exists (for faster execution times); and inform[ ]—Calling inform[sample["name",<Type>]→{experiments performed, or changes to a samples properties}] will upload the experimental information to the database, making sure not to repeat the upload if the inform statement is re-executed at any point with identical input.

Process Integration

A process is any preparative or analytical experiment that is performed on samples by any member of the lab, some resulting in the production of data as well as the altering of samples. Process handling is functional in nature, in that processes themselves are functions that operate with both inputs and outputs in the form of traditional computational inputs (integers, strings, etc.) as well other SLL objects, such as sample objects, data objects, and instrument objects.

For instance, the command:

sample["Pure Nearest Neighbor Sequence 5",DNA]= PrepHPLC[sample["Crude Nearest Neighbor Sequence 5"], Method→IonExchange, FlowRate→3 Milli Liter/Minute] is essentially directing the production of a new sample that results from the purification of crude nearest neighbor sequence 5 via preparative ion exchange HPLC run at 3 milliliter per minute flow rates. In this way processes are used to direct physical activity within a laboratory from within a lab notebook.

This can be implemented in the physical world though the use of process queues, for example. Initially, executing any process from within a notebook starts by adding samples and instructions involved in that process to a process queue. Process queues are lists of samples and instructions awaiting a given process. At any given time a process manager is assigned the responsibility of watching a process queue for a particular experiment, waiting until enough samples are on the queue that running a process (often in batch form) is most optimal, and then executing those processes, thereby removing the process from the queue and updating changes and additions to samples and data produced as a result of that process. Afterwards, the user who originally executed the process will be informed that the process has been completed, and now executing that line of code (the same line that placed an entry on the process queue previously), will return the results from that process (samples and/or data).

Furthermore, the experimental protocols for each process (SOPs) are stored in library files as code. When a process manager conducts a given experiment in the lab, these SOPs are presented to him or her as dynamic checklists on a computer, portable tablet, smartphone, or another remote device capable of information sharing. As the manager goes though the process, these checklists will present fields to mark completion of each step, enter information such as file-names from instruments, standard observations, or even detailed notes when running into unforeseen difficulties. These SOPs can also allow for integration with instrument programs, and any physical tracking devices, such as bar codes, or radio-frequency identification tags, for tracking source materials employed in the course of the experiment.

V. Computer Systems and Network

The methodology described here can be implemented on a computer system or network. A suitable computer system can include at least a processor and memory; optionally, a computer-readable medium that stores computer code for execution by the processor. Once the code is executed, the computer system carries out the described methodology.

In this regard, a "processor" is an electronic circuit that can execute computer programs. Suitable processors are exemplified by but are not limited to central processing units, microprocessors, graphics processing units, physics processing units, digital signal processors, network processors, front end processors, coprocessors, data processors and audio processors. The term "memory" connotes an electrical device that stores data for retrieval. In one aspect, therefore, a suitable memory is a computer unit that preserves data and assists computation. More generally, suitable methodology and devices can be used for providing the requisite network data transmission.

Also contemplated is a non-transitory computer readable medium that includes executable code for carrying out the described methodology. The medium also can contain data or databases needed for such methodology.

Embodiments can include program products comprising non-transitory machine-readable storage media for carrying or having machine-executable instructions or data structures stored thereon. Such machine-readable media may be any available media that may be accessed by a general purpose or special purpose computer or other machine with a processor. By way of example, such machine-readable storage media may comprise RAM, ROM, EPROM, EEPROM, CD-ROM or other optical disk storage, magnetic disk storage or other magnetic storage devices, or any other medium which may be used to store desired program code in the form of machine-executable instructions or data structures and which may be accessed by a general purpose or special purpose computer or other machine with a processor. Combinations of the above also come within the scope of "machine-readable media." Machine-executable instructions comprise, for example, instructions and data that cause a general purpose computer, special-purpose computer or special-purpose processing machine(s) to perform a certain function or group of functions.

Embodiments of the present invention have been described in the general context of method steps which may be implemented in one embodiment by a program product including machine-executable instructions, such as program code, for example in the form of program modules executed by machines in networked environments. Generally, program modules include routines, programs, logics, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As previously indicated, embodiments of the present invention may be practiced in a networked environment using logical connections to one or more remote computers having processors. Those skilled in the art will appreciate that such network computing environments may encompass many types of computers, including personal computers, hand-held devices, multi-processor systems, microprocessor-based or programmable consumer electronics, network PCs, minicomputers, mainframe computers, tablet computers, and cellular telephones. Embodiments of the invention also may be practiced in distributed and cloud computing environments where tasks are performed by local and remote processing devices that are linked, by hardwired links, by wireless links or by a combination of hardwired or wireless links, through a communications network. In a distributed computing environment, program modules may be located in both local and remote memory storage devices.

The present invention is further defined by reference to the following examples. It will be apparent to those skilled in the art that many modifications, both to threads and methods, may be practiced without departing from the scope of the current invention.

EXAMPLE 1

Instrumentation

The DNA synthesizer used here was a Bioautomation MerMade 192 (BioAutomation, Plano, Tex.) or an ABI 3900 (Advanced Biotechnologies Inc, Columbia, Md.). However, any DNA synthesizer could be used for this process, such as an ABI 392, ABI 394, Dr. Oligo, Digilab PolyPlex, or Polygen Industrial.

Reagents

All phosphoramidite reagents are purchased from Glen Research (Sterling, Va.) or Biosearch Technologies Inc (Novato, Calif.). Unless otherwise specified by the manufacturer, the phosphoramidites are dissolved in the appropriate amount of dry, biosynthesis grade acetonitrile (product number EM-AX0152-1 from VWR) to produce a 0.1 molar solution of the phosphoramidite. Bottles containing these solutions then are placed immediately on the synthesizer, to minimize the exposure time of the solution to air.

The reagents used for DNA synthesis are Activator Solution, Deblocking Solution, Cap A Solution, Cap B Solution, Oxidizer Solution, and anhydrous, biosynthesis-grade Acetonitrile. Activator Solution is typically either 0.45 M Tetrazole in acetonitrile, 0.25 M 5-Ethylthio-1H-tetrazole in acetonitrile, 0.25 M Dicyanoimidazole in acetonitrile, 5-Benzylthio-1H-tetrazole in acetonitrile or 0.25 M Saccharin 1-methylimidazole in acetonitrile. Deblocking Solution is typically 3% Trichloroacetic Acid in dichloromethane or 3% Dichloroacetic acid in dichloromethane. Cap A Solution is typically Tetrahydrofuran/Acetic anhydride/2,6-Lutidine (80/10/10) and Cap B Solution is typically 16% Methylimidazole in Tetrahydrofuran, although other reagent compositions are possible. Oxidizer Solution typically is 0.02 M Iodine in THF/Pyridine/Water (70/20/10), but it can be other mixtures, too, including 0.5 M camphorsulfonyloxaziridine in anhydrous acetonitrile. All of these reagents can be purchased from a number of suppliers, most notably VWR (Radnor, Pa.), EMD Chemical (Darmstadt, Germany), and Glen Research (Sterling, Va.).

UnySupport (200 nmole, 1000 Å) CPG (controlled pore glass) beads purchased from Glen Research were used as the solid supports for the DNA synthesis. Any commercially available or internally manufactured universal or standard support could be used here and at any scale. Illustrative examples of other suitable supports are UnyLinker Support CPGs and Universal Support III CPGs.

Cleavage and deprotection is performed most often with concentrated $NH_4OH$ (30% ammonium hydroxide). There are any number of solution and gas phase methods that can be used for oligonucleotide cleavage and deprotection.

Methodology

Oligonucleotides are synthesized on CPG beads, following standard protocols for the use of the particular synthesizer. Longer coupling times are typically used, as specified by the manufacturer, for modified phosphoramidites. Illustrative examples of modified phosphoramidites are 6-Fluorescein-phosphoramidite and 5'-Dabcyl phosphoramidite, although phosphoramidite options are not limited to these examples. After synthesis the oligonucleotides are cleaved from the solid support and deprotected pursuant to standard, published protocols, which can vary based on the particular phosphoramidites and modifications used in the synthesis of the oligonucleotide. Once the cleavage/deprotection step is complete, distilled water is added to the sample and the ammonium hydroxide (or other cleavage/deprotection reagent, depending on the monomers and modifications present in the oligonucleotide) is evaporated, leaving the crude oligonucleotide in water.

Purification and Desalting

In our batch process to produce DNA, the DNA samples are dried down after cleavage to meet the specifications of the high pressure liquid chromatography (HPLC) system. For the HPLC, a 9×250 mm DNA Pac-200 column on a Dionex UltiMate 3000 UHPLC (Thermo Scientific, Sunnyvale, Calif.) is used, with an autosampler and fraction collector. Through a number of optimization experiments, it has been determined that the optimal loading on this column is 50 nanomoles. Due to the limitations of the equipment, the maximum injection volume is 100 microliters. Using concentration and volume measurements, an injection volume can be calculated to get the required loading.

Since these specifications coincide with the crude yield of the sample itself, one needs to analyze the volume and the concentration of the sample before purification can start. To analyze the volume, a BioMicroLab Volume Check (BioMicroLab, Concord, Calif.) can be used, which performs liquid level detection on a 96 well plate. To analyze the concentration, this example performs a serial dilution of a small amount of the DNA sample into UV plates using a Gilson Quad-Z for pipetting. The example[huh?] then measures the absorbance of the wells in the UV plates using a BMG LabTech PHERAstar FS (BMG Labtech GmbH, Ortenberg, Germany), and from the absorbance, one can calculate the concentration of each sample.

For the HPLC this example runs each sample at 2.5 mL/min for 60 minutes with 40 mM Tris base, as the equilibration buffer, and 40 mM Tris base with 1.25 M NaCl, as the elution buffer. Buffer is prepared in-house and vacuum-filtered through a 0.22 µm filter. The gradient will differ based on the length of each strand, but a 20% to 50% linear gradient of the elution buffer is capable of resolving most strands at the typical length ranges. This combination of gradient, column, and long run time gives a single base pair (n, n−1) resolution and achieves maximum purity for the DNA, which is important in the construction of a translator and circuit. Fractions are collected by peak, and all fractions that correspond to the desired peaks and are from the same sample of oligonucleotide are combined and desalted in the next step of the process.

Desalting is done robotically using a Gilson GX-271 with 100 mM ammonium acetate as the equilibration buffer and 60% methanol in water (v/v) as the elution buffer. This example uses Waters SepPak-Vac 100 mg C18 cartridges (Waters Corporation, Milford, Mass.) as disposable columns for DNA binding. The cartridges initially are rinsed with 10 mL of elution buffer and then are flushed with 20 mL of MilliQ water. The cartridges are equilibrated using 10 mL of equilibration buffer, and HPLC fractions are combined and loaded into a cartridge. The cartridge is washed with 100 mL of MilliQ water, with a flow rate of 0.4 mL/min, and desalted samples are collected into a 96-well plate with 2 mL of elution buffer. This plate is placed under a needle dryer producing nitrogen gas to remove the methanol.

The pure volume and pure concentration is analyzed, using the same techniques stated above. From this point the DNA is sent off to quality control and, if it passes, on to one of the next steps of the process (annealing or conjugation). Alternatively, the DNA may be the final product.

Although the discussions above may refer to a specific order and composition of method steps, it is understood that the order of these steps may differ from what is described. For example, two or more steps may be performed concurrently or with partial concurrence. Also, some steps that are performed as discrete steps may be combined, steps being performed concurrently or in tandem may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present invention. Such variations will depend on the software and hardware systems chosen and on designer choice. It is understood that all such variations are within the scope of the invention. Likewise, software and web implementations of the present invention could be accomplished with standard programming techniques and logic to accomplish the various database searching steps, correlation steps, comparison steps and decision steps.

Unless otherwise defined, all technical and scientific terms used herein have the same meaning as what is commonly understood by one of ordinary skill in the art to which this invention belongs.

The inventions illustratively described herein may suitably be practiced in the absence of any element or elements, limitation or limitations, not specifically disclosed here. For example, the terms "comprising", "including," containing," etc. shall be read expansively and without limitation. Additionally, the terms and expressions employed here have been used as terms of description and not of limitation; hence, the use of such terms and expressions does not evidence an intention to exclude any equivalents of the features shown and described or of portions thereof. Rather, it is recognized that various modifications are possible within the scope of the invention claimed.

By the same token, while the present invention has been specifically disclosed by preferred embodiments and optional features, the knowledgeable reader will apprehend modification, improvement and variation of the subject matter embodied here. These modifications, improvements and variations are considered within the scope of the invention.

The invention has been described broadly and generically here. Each of the narrower species and subgeneric groupings falling within the generic disclosure also form part of the invention. This includes the generic description of the invention with a proviso or negative limitation removing any subject matter from the genus, regardless of whether or not the excised material is described specifically.

Where features or aspects of the invention are described by reference to a Markush group, the invention also is described thereby in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Although the invention has been described in conjunction with the above-mentioned embodiments, the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A system for preparing a chimeric oligonucleotide, comprising at least two instruments and program code which, when executed, configures the system to:
   (a) synthesize a first nucleic acid (NA) oligonucleotide and a second peptide nucleic acid (PNA) oligonucleotide, thereby providing a first sample of the first oligonucleotide and a second sample of the second oligonucleotide;
   (b) determine the volume of each sample, the concentration of the oligonucleotide in each sample and whether each oligonucleotide has a secondary structure;
   (c) subject each oligonucleotide to chromatography under conditions suitable for disrupting the secondary structure of the oligonucleotide if the oligonucleotide has a secondary structure, and achieving single base-resolution for each oligonucleotide, wherein the conditions are a function of the volume and/or concentration measured in step (b);
   (d) collect each oligonucleotide from the chromatography; and
   (e) conjugate the first oligonucleotide to the second oligonucleotide to form a chimeric oligonucleotide.

2. The system of claim 1, wherein the instruments are interconnected.

3. The system of claim 1, wherein the instruments are connected to a central computer.

4. The system of claim 3, wherein the instruments access a data file or a database at the central computer.

5. The system of claim 3, wherein the instruments are controllable by the central computer.

6. The system of claim 1, wherein the system is further configured to desalt and dry the chimeric oligonucleotide and to dissolve the chimeric oligonucleotide in a buffer or solvent.

7. The system of claim 1, wherein step (b) further comprises determining the properties of each of the oligonucleotides, where the properties are selected from chemical composition, number of bases, presence or absence of linkers, and modifications.

8. The system of claim 1, wherein the system is further configured to introduce a modification to at least one of the oligonucleotides.

9. The system of claim 8, wherein the modification comprises addition of one or more selected from the group consisting of a fluorescent molecule, a fluorescence quenching molecule, a non-standard base, a non-nucleic acid based molecule, and a functional group.

10. The system of claim 1, wherein the system is further configured to remove a protection group from at least one of the oligonucleotides, wherein the protection group is added during synthesis or is part of the individual monomers used as reactants in the synthesis.

11. The system of claim 10, wherein the protection group is selected from the group consisting of acetyl (Ac), benzoyl (Bz), isobutyryl (iBu), dimethylformamidine (dmf), pivaloyl (Piv), benzhydryloxycarbonyl (Bhoc), fluorenylmethyloxycarbonyl (Fmoc), tert-butyloxycarbonyl (Boc), carboxybenzyl (Cbz), 2-chlorocarboxybenzyl (2-Cl-Cbz), trityl (Trt), methoxytrityl (Mtr), pentamethyldihydrobenzofuran (Pbf), S-tert-butyl (S-tBu), acetamidomethyl (Acm), and tert-butyl (tBu).

12. The system of claim 1, wherein the conjugation involves a linker that facilitates the formation of one or more covalent bonds between the first oligonucleotide and the second oligonucleotide.

13. The system of claim 1, wherein the system is further configured to pass the chimeric oligonucleotide through chromatography under conditions suitable for separating the chimeric oligonucleotide from unconjugated first and second oligonucleotides.

14. The system of claim 1, wherein the chromatography is high pressure liquid chromatography (HPLC), medium pressure liquid chromatography, low pressure liquid chromatography or fast protein liquid chromatography (FPLC).

15. The system of claim 1, wherein the program code is coded in a symbolic lab language.

16. The system of claim 15, wherein the symbolic lab language specifies workflow management that comprises sample tracking, data management and manipulation, instrument management, and conditional analysis of the process.

17. The system of claim 1, wherein each oligonucleotide is represented as a sample object by the program code.

18. The system of claim 1, wherein the determined volume, concentration and secondary structure is represented as a data object by the program code.

19. A method for preparing a chimeric oligonucleotide, comprising operating at least two instruments controlled by program code which configures the instruments to:
   (a) synthesize a first nucleic acid (NA) oligonucleotide and a second peptide nucleic acid (PNA) oligonucleotide, thereby providing a first sample of the first oligonucleotide and a second sample of the second oligonucleotide;
   (b) determine the volume of each sample, the concentration of the oligonucleotide in each sample and whether each oligonucleotide has a secondary structure;
   (c) subject each oligonucleotide to chromatography under conditions suitable for disrupting the secondary structure of the oligonucleotide if the oligonucleotide has a secondary structure, and achieving single base-resolution for each oligonucleotide, wherein the conditions are a function of the volume and/or concentration measured in step (b);
   (d) collect each oligonucleotide from the chromatography; and
   (e) conjugate the first oligonucleotide to the second oligonucleotide to form a chimeric oligonucleotide.

* * * * *